(12) United States Patent
Huang et al.

(10) Patent No.: US 7,214,427 B2
(45) Date of Patent: May 8, 2007

(54) COMPOSITE BEADS COMPRISING MAGNETIZABLE SUBSTANCE AND ELECTRO-CONDUCTIVE SUBSTANCE

(75) Inventors: Mingxian Huang, San Diego, CA (US); Lei Wu, San Diego, CA (US); Xiaobo Wang, San Diego, CA (US); Junquan Xu, San Diego, CA (US); Guo Liang Tao, San Diego, CA (US); Jing Cheng, Beijing (CN)

(73) Assignee: Aviva Biosciences Corporation, San Diego, CA (US)

( * ) Notice: Subject to any disclaimer, the term of this patent is extended or adjusted under 35 U.S.C. 154(b) by 621 days.

(21) Appl. No.: 10/104,579

(22) Filed: Mar. 21, 2002

(65) Prior Publication Data
US 2003/0178309 A1 Sep. 25, 2003

(51) Int. Cl.
*B32B 5/16* (2006.01)

(52) U.S. Cl. ............ 428/402; 428/403; 428/900; 424/489; 424/639; 424/646; 424/617

(58) Field of Classification Search ............ 428/402, 428/403, 900; 435/6, 7.1; 436/172, 546, 436/2; 424/489, 639, 646, 617
See application file for complete search history.

(56) References Cited

U.S. PATENT DOCUMENTS

| | | | |
|---|---|---|---|
| 4,010,242 A | 3/1977 | Iler et al. | 423/335 |
| 4,285,819 A | 8/1981 | Yen et al. | 210/679 |
| 4,336,173 A | 6/1982 | Ugelstad | 523/205 |
| 4,421,660 A | 12/1983 | Solc nee Hajna | 252/62.54 |
| 4,490,436 A | 12/1984 | Kawakami et al. | 428/403 |
| 4,554,088 A | 11/1985 | Whitehead et al. | 252/62.54 |
| 4,582,622 A | 4/1986 | Ikeda et al. | 660/462 |
| 4,654,267 A | 3/1987 | Ugelstad et al. | 428/407 |
| 4,774,265 A | 9/1988 | Ugelstad et al. | 521/55 |
| 4,795,698 A | 1/1989 | Owen et al. | 435/4 |
| 4,965,007 A | 10/1990 | Yudelson | 252/62.53 |
| 5,091,206 A | 2/1992 | Wang et al. | 427/2 |
| 5,232,789 A | 8/1993 | Platz et al. | 428/637 |
| 5,283,079 A | 2/1994 | Wang et al. | 427/2 |
| 5,318,797 A | 6/1994 | Matijevic et al. | 427/213.31 |
| 5,346,791 A * | 9/1994 | Ozawa et al. | 430/111.32 |
| 5,395,688 A | 3/1995 | Wang et al. | 428/327 |

(Continued)

FOREIGN PATENT DOCUMENTS

JP 09-143502 6/1997

(Continued)

OTHER PUBLICATIONS

U.S. Appl. No. 09/636,104, filed Aug. 10, 2000, Wang et al.

(Continued)

*Primary Examiner*—H. Thi Le
(74) *Attorney, Agent, or Firm*—Morrison & Foerster LLP; Kristin Eaton

(57) ABSTRACT

This invention relates generally to the field of moiety or molecule isolation, detection and manipulation and library synthesis. In particular, the invention provides a bead, which bead comprises: a) a magnetizable substance; and b) an electrically conductive substance or an optical labeling substance. Methods and kits for isolating, detecting and manipulating moieties and synthesizing libraries using the beads are also provided.

25 Claims, 3 Drawing Sheets

U.S. PATENT DOCUMENTS

| | | | |
|---|---|---|---|
| 5,648,124 A | 7/1997 | Sutor | 427/475 |
| 5,744,367 A * | 4/1998 | Talley et al. | 436/172 |
| 5,785,913 A * | 7/1998 | Clark et al. | 264/109 |
| 5,795,470 A | 8/1998 | Wang et al. | 210/222 |
| 5,834,121 A | 11/1998 | Sucholeiki et al. | 428/407 |
| 6,114,038 A | 9/2000 | Castro et al. | 428/402.24 |
| 6,127,132 A | 10/2000 | Breitling et al. | 435/7.1 |
| 6,134,413 A * | 10/2000 | Asanae et al. | 399/267 |
| 6,174,708 B1 | 1/2001 | Sodoyer et al. | 435/91.1 |
| 6,214,560 B1 | 4/2001 | Yguerabide et al. | 356/417 |
| 6,252,664 B1 | 6/2001 | Barbera-Guillem | 435/7.1 |
| 6,268,222 B1 * | 7/2001 | Chandler et al. | 436/523 |
| 6,284,470 B1 * | 9/2001 | Bitner et al. | 435/6 |
| 6,306,610 B1 * | 10/2001 | Bawendi et al. | 435/7.1 |
| 6,548,171 B1 * | 4/2003 | Barbera-Guillem et al. | 428/402.24 |
| 6,773,812 B2 * | 8/2004 | Chandler et al. | 428/403 |
| 6,806,050 B2 | 10/2004 | Zhou et al. | |
| 2002/0164271 A1 | 11/2002 | Ho | |

FOREIGN PATENT DOCUMENTS

| | | |
|---|---|---|
| JP | 09-184842 | 7/1997 |

OTHER PUBLICATIONS

U.S. Appl. No. 09/679,024, filed Oct. 4, 2000, Wang et al.
U.S. Appl. No. 09/924,428, filed Aug. 7, 2001, Wu et al.
Bleaney, B.I and Bleaney, B. (1975). Chapter 6 *In* Electricity and Magnetism. Oxford., pp. 169-174.
Bleaney, B.I and Bleaney, B. (1975). Chapter 16 *In* Electricity and Magnetism. Oxford., pp. 519-524.
Bruchez et al. (1998). Science 281:2013-2015.
Chan and Nie (1998). Science 281:2016-2018.
Cheng et al (1998). Nature Biotechnology 16:541-546.
Goater, A.D. and Pethig, R. (1998). Parasitology 117:S177-89.
Han et al. (2001). Nature Biotechnology 19:631-635.
Lichtenberg et al (2000). Micro Total Analysis Systems 2000, pp. 307-310.
Matijevic (1981). Acc. Chem. Res. 14:22-29.
Pethig, R. and Markx, G.H. (1997). Trends Biotechnol. 15(10):426-32.
Wang et al. (1997). Biophys. J. 72:1887-1899.
Wang et al. (1997). IEEE Transaction on Industry Applications 33(3):660-669.

* cited by examiner

COMPOSITE BEADS COMPRISING MAGNETIZABLE SUBSTANCE AND ELECTRO-CONDUCTIVE SUBSTANCE

TECHNICAL FIELD

This invention relates generally to the field of moiety or molecule isolation, detection and manipulation and library synthesis. In particular, the invention provides a bead, which bead comprises: a) a magnetizable substance; and b) an electrically conductive substance or an optical labeling substance. Methods and kits for isolating, detecting and manipulating moieties and synthesizing libraries using the beads are also provided.

BACKGROUND ART

The preparation and use of magnetically responsive beads are known in the art. See. e.g., U.S. Pat. Nos. 4,285,819, 4,582,622, 4,795,698, 5,091,206, 5,795,470, 5,648,124, and 5,834,121. Carbon beads have been used as HPLC packing materials and coating filler. Quantum dots have found their applications in bioanalysis just recently. Quantum dot nanocrystals are nanometer scale particles that are neither small molecules nor bulk solids. Their composition and small size (a few hundred to a few thousand atoms) give these dots extraordinary optical properties, which can be readily customized by changing the size or composition of the dots. This property is the basis for encoding using quantum dots.

Microarray, biochips, and high throughput bioassays have experienced rapid progress during last several years. There are two types of biochips: passive and active biochips. Passive biochips refer to those on which chemical or biochemical reactions are dependent on passive diffusion of sample molecules. Active biochips, on the other hand, allow versatile functions of molecular manipulation, interaction, hybridization reaction and separation by external forces through means such as microfluidic manipulation and electrical manipulation of molecules. When functional beads are used as molecular carrier, the beads are manipulated on the active chips.

Although beads technology has found wide applications in separation and analysis, there is a limited supply of various beads, especially those suitable to be used with active biochips, e.g., multiple-forces chips. The present invention addresses this and other related needs in the art.

DISCLOSURE OF THE INVENTION

In one aspect, the present invention is directed to a bead, which bead comprises:

a) a magnetizable substance; and b) an electrically conductive substance or an optical labeling substance.

In another aspect, the present invention is directed to a method for isolating a moiety, which method comprises: a) providing a bead comprising 1) a magnetizable substance, 2) an optical labeling substance, and preferably 3) a binding partner that is capable of binding to a moiety to be isolated; b) contacting a sample containing or suspected of containing of said moiety with said bead provided in step a) under conditions allowing binding between said moiety and said bead and/or binding partner; and c) recovering said bead from said sample, whereby the identity of said isolated moiety is assessed by analyzing said optical labeling substance comprised in said bead.

In still another aspect, the present invention is directed to a method for manipulating a moiety, which method comprises: a) providing a bead comprising 1) a magnetizable substance, 2) an electrically conductive substance, and preferably 3) a binding partner that is capable of binding to a moiety to be manipulated; b) coupling said moiety to said bead provided in step a) via binding between said moiety and said binding partner to form a moiety-bead complex; and c) manipulating said moiety-bead complex with a dielectrophoresis, a traveling-wave dielectrophoresis and/or a magnetic force, preferably in a chip format, thereby said moiety is manipulated. The above method for manipulating a moiety can be readily extended to manipulating multiple moieties by using multiple types of beads, each type of which is targeted to one type of moieties to be manipulated.

In yet another aspect, the present invention is directed to a kit for manipulating a moiety, which kit comprises: a) a bead comprising 1) a magnetizable substance, 2) an electrically conductive substance or an optical labeling substance, and preferably 3) a binding partner that is capable of binding, or capable of specifically binding, to a moiety to be manipulated; and b) a means for generating a physical force for manipulating said moiety-bead complex.

In yet another aspect, the present invention is directed to a kit for manipulating a moiety in a chip format, which kit comprises: a) a bead comprising 1) a magnetizable substance, 2) an electrically conductive substance or an optical labeling substance, and preferably 3) a binding partner that is capable of binding, or capable of specifically binding, to a moiety to be manipulated; and b) a chip on which a moiety-bead complex can be manipulated.

In yet another aspect, the present invention is directed to a method for detecting a moiety, which method comprises: a) providing a bead comprising 1) a magnetizable substance, 2) an optical labeling substance, and preferably 3) a binding partner that is capable of binding to a moiety to be detected; b) contacting a sample containing or suspected of containing of said moiety with said bead provided in step a) under conditions allowing binding between said moiety and said bead and/or said binding partner; and c) detecting binding between said moiety and said bead and/or said binding partner, whereby the presence or amount of said moiety is assessed by analysis of binding between said moiety and said bead and/or said binding partner and the identity of said moiety is assessed by analyzing the optical labeling substance comprised in the bead. The above method for detecting a moiety can be readily extended to detecting multiple moieties by using multiple types of beads, each type of which is targeted to one type of moieties to be detected and each of which has a unique optical labeling substance.

In yet another aspect, the present invention is directed to a method for synthesizing a library, which method comprises: a) providing a plurality of beads of the present invention, each of said beads comprising a magnetizable substance and an optical labeling substance that corresponds to an entity to be synthesized on said bead; and b) synthesizing said entities on said beads, wherein said beads are sorted after each synthesis cycle according to said optical labeling substances and the sorted beads are then subjected to appropriate synthesis reaction in the next synthesis cycle according to said entities to be synthesized on said beads, whereby a library is synthesized, wherein each of said beads contains an entity that corresponds to an optical labeling substance on said bead and the sum of said beads collectively contains a plurality of entities that is predetermined before the library synthesis. A library that is synthesized according to the above method is also provided.

In yet another aspect, the present invention is directed to a method for synthesizing a library, which method comprises: a) providing a plurality of beads, each of said beads comprising a magnetizable substance, an electrically conductive substance and a unique optical labeling substance, wherein said unique optical labeling substance on each of said beads corresponds to an entity to be synthesized on each of said beads; and b) synthesizing said entities on said beads, wherein said beads are identified after each synthesis cycle according to said unique optical labeling substances, whereby a library is synthesized, wherein each of said beads contains an entity that corresponds to said unique optical labeling substance on each of said beads.

In yet another aspect, the present invention is directed to a method for generating an antibody library, which method comprises: a) contacting a library synthesized according to the above method with a plurality of antibodies; and b) selecting and/or recovering the antibodies that specifically bind to the entities of the above library.

MODES OF CARRYING OUT THE INVENTION

Figure 1:
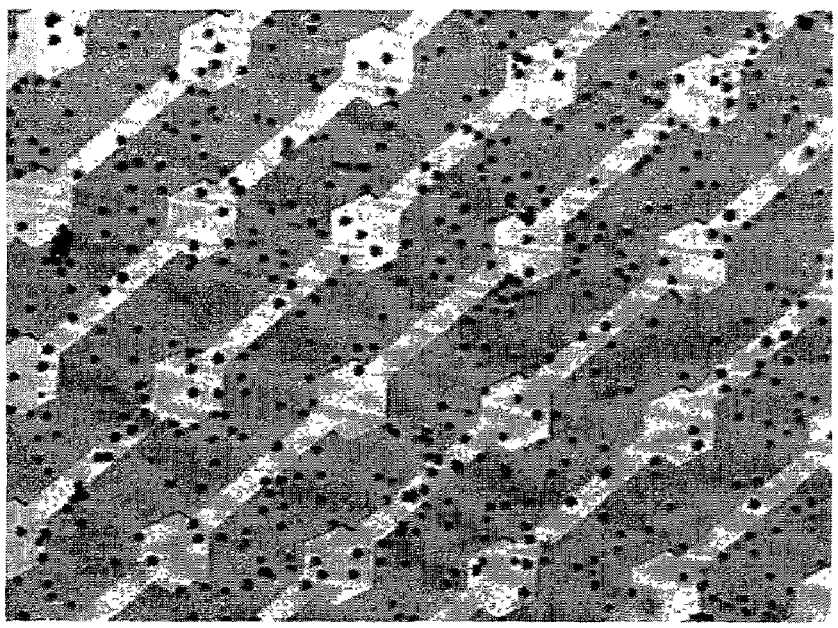
FIG. 1 shows the random distribution of exemplary beads (or microbeads) of the present invention on a microelectrode array. These microbeads can exhibit magnetic field induced effects, and positive and negative dielectrophoresis effects. The microbeads are seen as black dots, the microelectrodes are seen as the light structure and the grey area represents the inter-microelectrode space.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "magnetic substance" refers to any substance that has the properties of a magnet, pertaining to a magnet or to magnetism, producing, caused by, or operating by means of, magnetism.

As used herein, "magnetizable substance" refers to any substance that has the property of being interacted with the field of a magnet, and hence, when suspended or placed freely in a magnetic field, of inducing magnetization and producing a magnetic moment. Examples of magnetizable substances include, but are not limited to, paramagnetic, ferromagnetic and ferrimagnetic substances.

As used herein, "paramagnetic substance" refers to the substances where the individual atoms, ions or molecules possess a permanent magnetic dipole moment. In the absence of an external magnetic field, the atomic dipoles point in random directions and there is no resultant magnetization of the substances as a whole in any direction. This random orientation is the result of thermal agitation within the substance. When an external magnetic field is applied, the atomic dipoles tend to orient themselves parallel to the field, since this is the state of lower energy than antiparallel position. This gives a net magnetization parallel to the field and a positive contribution to the susceptibility. Further details on "paramagnetic substance" or "paramagnetism" can be found in various literatures, e.g., at Page 169–page 171, Chapter 6, in "Electricity and Magnetism" by B. I Bleaney and B. Bleaney, Oxford, 1975.

As used herein, "ferromagnetic substance" refers to the substances that are distinguished by very large (positive) values of susceptibility, and are dependent on the applied magnetic field strength. In addition, ferromagnetic substances may possess a magnetic moment even in the absence of the applied magnetic field, and the retention of magnetization in zero field is known as "remanence". Further details on "ferromagnetic substance" or "ferromagnetism" can be found in various literatures, e.g., at Page 171–page 174, Chapter 6, in "Electricity and Magnetism" by B. I Bleaney and B. Bleaney, Oxford, 1975.

As used herein, "ferrimagnetic substance" refers to the substances that show spontaneous magnetization, remanence, and other properties similar to ordinary ferromagnetic materials, but the spontaneous moment does not correspond to the value expected for full parallel alignment of the (magnetic) dipoles in the substance. Further details on "ferrimagnetic substance" or "ferrimagnetism" can be found in various literatures, e.g., at Page 519–524, Chapter 16, in "Electricity and Magnetism" by B. I Bleaney and B. Bleaney, Oxford, 1975.

As used herein, "metal oxide particle" refers to any oxide of a metal in a particle form. Certain metal oxide particles have paramagnetic or super-paramagnetic properties. "Paramagnetic particle" is defined as a particle which is susceptible to the application of external magnetic fields, yet is unable to maintain a permanent magnetic domain. In other words, "paramagnetic particle" may also be defined as a particle that is made from or made of "paramagnetic substances". Non-limiting examples of paramagnetic particles include certain metal oxide particles, e.g., $Fe_3O_4$ particles, metal alloy particles, e.g., CoTaZr particles.

As used herein, "electrically conductive substance" refers to any substance that is not electrically-insulating and can exhibit positive dielectrophoresis force under appropriate conditions. Under such conditions, "electrically conductive substance" has higher electrical conductivity and/or higher dielectric permittivity than those of the suspending media in which the "electrically conductive substance" is suspended, placed, or introduced.

As used herein, "optical labeling substance" refers to any optically detectable substance that can be used to label the beads of the present invention to facilitate and/or enable detection and/or identification of the beads. Quantum-dot is an example of an optical labeling substance.

As used herein, "scattered-light detectable particle" refers to any particle that can emit unique and identifiable scattered-light upon illumination with light under appropriate conditions. The nano-sized particles with certain "resonance light scattering (RLS)" properties are examples of one type of "scattered-light detectable particle."

As used herein, "quantum dot" refers to a fluorescent label comprising water-soluble semiconductor nanocrystal(s). One unique feature of a quantum dot is that its fluorescent spectrum is related to or determined by the diameter of its nanocrystals(s). "Water-soluble" is used herein to mean sufficiently soluble or suspendable in a aqueous-based solution, such as in water or water-based solutions or physiological solutions, including those used in the various fluorescence detection systems as known by those skilled in the art. Generally, quantum dots can be prepared which result in relative monodispersity; e.g., the diameter of the core varying approximately less than 10% between quantum dots in the preparation. Details of quantum dots and how they can be incorporated into microbeads may be found in the literatures, for example, in the articles by Chan and Nie, *Science*, 281:2016 (1998) and by Han et al., *Nature Biotechnology*, 19:631–635 (2001).

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces.

As used herein, a "chamber" refers to a structure that comprises a chip and that is capable of containing a fluid sample. The chamber may have various dimensions and its volume may vary between 0.001 microliter and 50 milliliter. More detailed description of a chamber is given in Section C.

As used herein, "a means for generating a physical force on said chip" refers to any substance, structure or a combination thereof that is capable of generating, in conjunction with an internal structure on a chip, to generate a desirable physical force on the chip.

As used herein, "physical field," e.g., used itself or used as "physical field in a region of space" or "physical field is generated in a region of space" means that the region of space has following characteristics. When a moiety, alone or bound to a bead via a binding partner, of appropriate properties is introduced into the region of space (i.e. into the physical field), forces are produced on the moiety, the bead or both, as a result of the interaction between the moiety and/or bead and the field. A moiety can be manipulated within a field via the physical forces exerted on the moiety by the field.

Exemplary fields include electric, magnetic, acoustic, optical and velocity fields. In the present invention, physical field always exists in a medium in a region of space, and the moiety is suspended in, or is dissolved in, or more generally, is placed in the medium. Typically, the medium is a fluid such as aqueous or non-aqueous liquids, or a gas. Depending on the field configuration, an electric field may produce electrophoretic forces on charged moieties, or may produce conventional dielectrophoretic forces and/or traveling wave dielectrophoretic forces on charged and/or neutral moieties. Magnetic field may produce magnetic forces on magnetic moieties. Acoustic field may produce acoustic radiation forces on moieties. Optical field may produce optical radiation forces on moieties. Velocity field in the medium in a region of space refers to a velocity distribution of the medium that moves in the region of the space. Various mechanisms may be responsible for causing the medium to move and the medium at different positions may exhibit different velocities, thus generating a velocity field. Velocity field may exert mechanical forces on moieties in the medium.

As used herein, "medium (or media)" refers to a fluidic carrier, e.g. liquid or gas, wherein a moiety, alone or bound to a bead via a binding partner, is dissolved, suspended or contained.

As used herein, "microfluidic application" refers to the use of microscale devices, e.g., the characteristic dimension of basic structural elements is in the range between less than 1 micron to 1 cm scale, for manipulations and processes in a fluidic setting, typically for performing specific biological, biochemical or chemical reactions and procedures. The specific areas include, but are not limited to, biochips, i.e., chips for biologically related reactions and processes, chemchips, i.e., chips for chemical reactions, or a combination thereof. The characteristic dimensions of the basic elements refer to the single dimension sizes. For example, for the microscale devices having circular shape structures (e.g. round electrode pads), the characteristic dimension refers to the diameter of the round electrodes. For the devices having thin, rectangular lines as basic structures, the characteristic dimensions may refer to the width or length of these lines.

As used herein, "built-in structures on said substrate of a chip" means that the structures are built into the substrate or the structures are located on the substrate or the structures are structurally linked to the substrate of the chip. In one embodiment, the built-in structures may be fabricated on the substrate. For example, as described in "Dielectrophoretic manipulation of cells using spiral electrodes by Wang et al.,

*Biophys. J.,* 72:1887–1899 (1997)", spiral electrodes are fabricated on a glass substrate. Here the spiral electrodes are "built-in" structures on the glass substrate. In another embodiment, the "built-in" structures may be first fabricated on one substrate and the structure-containing first substrate may then be attached or bound to a second substrate. Such structures are "built-in" structures not only on the first substrate but also on the second substrate. In still another embodiment, the built-in structures may be attached or bound to the substrate. For example, thin, electrically-conductive wires may be used as electrodes for producing electric field. These electric wires may be bound or attached to a glass substrate. In this case, the electrically-conductive wires are "built-in" structures on the glass substrate. Throughout this application, when it is described that "built-in" structures on the chip or on the substrate are capable of generating physical forces and/or physical fields or these structures generate physical forces and/or physical fields, these structures are used in combination with external signal sources or external energy sources.

As used herein, "structures internal to said apparatus" means that the structures are integral parts of and structurally linked to other parts of the apparatus, or the structures are not separated or separable from other structural elements of the apparatus. For example, such internal structures can be microfabricated or otherwise attached to the substrate or other structural element(s) of the apparatus. Any "built-in structures on said substrates" described above are "structures internal to said apparatus" as long as the said apparatus comprise the substrates. Any built-in structures on a chip are "structures internal to said apparatus" as long as the said apparatus comprise the chip. Throughout this application, when it is described that "internal" structures of apparatus are capable of generating physical forces and/or physical fields or these structures generate physical forces and/or physical fields, these structures are used in combination with external signal sources or external energy sources.

As used herein, "micro-scale structures" means that the scale of the internal structures of the apparatus for exerting desired physical forces must be compatible with and useable in microfluidic applications and have characteristic dimension of basic structural elements in the range from about 1 micron to about 20 mm scale.

As used herein, "moiety" refers to any substance whose isolation, manipulation, measurement, quantification or detection using the present bead is desirable. Normally, the dimension (or the characteristic dimensions) of the moiety should not exceed 1 cm. For example, if the moiety is spherical or approximately spherical, the dimension of the moiety refers to the diameter of the sphere or an approximated sphere for the moiety. If the moiety is cubical or approximately cubical, then the dimension of the moiety refers to the side width of the cube or an approximated cube for the moiety. If the moiety has an irregular shape, the dimension of the moiety may refer to the average between its largest axis and smallest axis. Non-limiting examples of moieties include cells, cellular organelles, viruses, particles, molecules, e.g., proteins, DNAs and RNAs, or an aggregate or complex thereof.

Moiety to be isolated, manipulated, measured, quantified or detected includes many types of particles—solid (e.g., glass beads, latex particles, magnetic beads), liquid (e.g., liquid droplets) or gaseous particles (e.g., gas bubble), dissolved particles (e.g., molecules, proteins, antibodies, antigens, lipids, DNAs, RNAs, molecule-complexes), suspended particles (e.g., glass beads, latex particles, polystyrene beads). Particles can be organic (e.g., mammalian cells or other cells, bacteria, virus, or other microorganisms) or inorganic (e.g., metal particles). Particles can be of different shapes (e.g., sphere, elliptical sphere, cubic, discoid, needle-type) and can be of different sizes (e.g. nano-meter-size gold sphere, to micrometer-size cells, to millimeter-size particle-aggregate). Examples of particles include, but not limited to, biomolecules such as DNA, RNA, chromosomes, protein molecules (e.g., antibodies), cells, colloid particles (e.g., polystyrene beads, magnetic beads), any biomolecules (e.g., enzyme, antigen, hormone etc). One specific type of particle refers to complexes formed between moieties and their binding partners, as described in a co-pending US Patent application entitled "METHODS FOR MANIPULATING MOIETIES IN MICROFLUIDIC SYSTEMS" (U.S. patent application Ser. No. 09/636,104, by Wang et al., filed on Aug. 10, 2000). The examples of such complexes include particle-particle complexes, particle-molecule complexes (e.g., cell-magnetic bead complexes formed by binding of the cells onto antibody-coated beads through the interaction between the antigens or protein molecules on cell surfaces and the antibody molecules immobilized on the magnetic bead surfaces; DNA molecule-magnetic bead complexes formed by immobilizing DNA molecules on magnetic bead surfaces, or protein molecule-polystyrene bead complexes formed by covering polystyrene bead surfaces with protein molecules). The methods disclosed in a co-pending US patent application "METHODS FOR MANIPULATING MOIETIES IN MICROFLUIDIC SYSTEMS" (U.S. patent application Ser. No. 09/636,104, by Wang et al., filed on Aug. 10, 2000) may be used for manipulating moieties and/or binding partner-moiety complexes in the devices and apparatus in the present invention. The co-pending US patent application "METHODS FOR MANIPULATING MOIETIES IN MICROFLUIDIC SYSTEMS" (U.S. patent application Ser. No. 09/636,104) by Wang et al, filed on Aug. 10, 2000 is incorporated by reference in their entirety. These moieties can be isolated, manipulated, measured, quantified or detected using a bead of the present application.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "binding partners" refers to any substances that bind to the moieties with desired affinity or specificity. Non-limiting examples of the binding partners include cells, cellular organelles, viruses, particles, microparticles or an aggregate or complex thereof, or an aggregate or complex of molecules, or specific molecules such as antibodies, single stranded DNAs. The binding partner can be a substance that is coated on the surface of a bead. Alternatively, the binding partner can be a substance that is incorporated, e.g., microfabricated, into the material composition of a bead. The material composition of a bead may possess binding affinity to certain moiety, and thus functioning a binding partner itself.

As used herein, "an element that facilitates and/or enables manipulation of the bead and/or a moiety/bead complex" refers to any substance that is itself manipulatable or makes the moiety/bead complex manipulatable with the desired physical force(s). Non-limiting examples of the elements include cells, cellular organelles, viruses, particles, microparticles or an aggregate or complex thereof, or an aggregate or complex of molecules. Non-limiting examples of the elements may further include deposited or other-procedure-produced materials with specific physical or chemical properties. Various metal compositions such as Au, Cr, Ti, Pt etc are examples of the elements that can be incorporated into the beads and increase electrical conductivity of the beads. Other conductive materials such as carbon and/or conductive polymers can also be incorporated into the beads to increase electrical conductivity of the beads. Insulating materials such as polystyrene, paralene, or other plastic polymers are also examples of the elements that may be incorporated into the beads and reduce electrical conductivity of the beads.

As used herein, "microparticles" refers to particles of any shape, any composition, any complex structures that are manipulatable by desired physical force(s) in microfluidic settings or applications. One example of microparticles is magnetic beads that are manipulatable by magnetic forces. Another example of microparticles is a cell that is manipulatable by an electric force such as a traveling-wave dielectrophoretic force. The microparticles used in the methods can have a dimension from about 0.01 micron to about ten centimeters. Preferably, the microparticles used in the methods have a dimension from about 0.01 micron to about several thousand microns. Examples of the microparticles include, but are not limited to, plastic particles, polystyrene microbeads, glass beads, magnetic beads, hollow glass spheres, particles of complex compositions, microfabricated free-standing microstructures, etc. Other particles include cells, cell organelles, large biomolecules such as DNA, RNA and proteins etc.

As used herein, "manipulation" refers to moving or processing of the moieties and the beads disclosed in the present invention, which results in one-, two- or three-dimensional movement of the moiety (and the beads), in a chip format, whether within a single chip or between or among multiple chips, or on a substrate or among substrates of an apparatus. "Manipulation" of moieties and the beads can also be performed in a non-chip format, e.g., in liquid containers. Non-limiting examples of the manipulations include transportation, focusing, enrichment, concentration, aggregation, trapping, repulsion, levitation, separation, sorting, fractionation, isolation or linear or other directed motion of the moieties. For effective manipulation, the characteristics of the moiety (and the beads) to be manipulated and the physical force used for manipulation must be compatible. For example, the beads with certain magnetic properties can be used with magnetic force. Similarly, the beads with electric charge(s) can be used with electrostatic (i.e. electrophoretic) force. In the case of manipulating beads-binding partner-moiety complexes, the characteristics of the moiety, or its binding partner or the beads, and the physical force used for manipulation must be compatible. For example, moiety or its binding partner or the beads with certain dielectric properties to induce dielectric polarization in the moiety or its binding partner or the beads can be used with dielectrophoresis force.

As used herein, "the moiety is not directly manipulatable" by a particular physical force means that no observable movement of the moiety can be detected when the moiety itself not coupled to a binding partner is acted upon by the particular physical force.

As used herein, "physical force" refers to any force that moves the moieties or their binding partners or the corresponding beads without chemically or biologically reacting with the moieties and the binding partners, or with minimal chemical or biological reactions with the binding partners and the moieties so that the biological/chemical functions/ properties of the binding partners and the moieties are not substantially altered as a result of such reactions. Throughout the application, the term of "forces" or "physical forces" always means the "forces" or "physical forces" exerted on a moiety or moieties, the binding partner(s) and/or the bead(s). The "forces" or "physical forces" are always generated through "fields" or "physical fields". The forces exerted on moieties, the binding partner(s) and/or the bead(s) by the fields depend on the properties of the moieties, the binding partner(s) and/or the bead(s). Thus, for a given field or physical field to exert physical forces on a moiety, it is necessary for the moiety to have certain properties. While certain types of fields may be able to exert forces on different types of moieties having different properties, other types of fields may be able to exert forces on only limited type of moieties. For example, magnetic field can exert forces or magnetic forces only on magnetic particles or moieties having certain magnetic properties, but not on other particles, e.g., polystyrene beads. On the other hand, a non-uniform electric field can exert physical forces on many types of moieties such as polystyrene beads, cells, and also magnetic particles. It is not necessary for the physical field to be able to exert forces on different types of moieties or different moieties. But it is necessary for the physical field to be able to exert forces on at least one type of moiety or at least one moiety, the binding partner(s) and/or the bead(s).

As used here in, "electric forces (or electrical forces)" are the forces exerted on moieties, the binding partner(s) and/or the bead(s) by an electric (or electrical) field.

As used herein, "magnetic forces" are the forces exerted on moieties, the binding partner(s) and/or the bead(s) by a magnetic field.

As used herein, "acoustic forces (or acoustic radiation forces)" are the forces exerted on moieties, the binding partner(s) and/or the bead(s) by an acoustic field.

As used herein, "optical (or optical radiation) forces" are the forces exerted on moieties, the binding partner(s) and/or the bead(s) by an optical field.

As used herein, "mechanical forces" are the forces exerted on moieties, the binding partner(s) and/or the bead(s) by a velocity field.

As used herein, "the moiety to be manipulated is substantially coupled onto surface of the binding partner" means that a certain percentage, and preferably a majority, of the moiety to be manipulated is coupled onto surface of the binding partner and can be manipulated by a suitable physical force via manipulation of the binding partner in the microdevice. Ordinarily, at least 0.5% of the moiety to be manipulated is coupled onto surface of the binding partner. Preferably, at least 1%, 2%, 3%, 4%, 5%, 10%, 20%, 30%, 40%, 50%, 60%, 70%, 80% or 90% of the moiety to be manipulated is coupled onto surface of the binding partner. The percentage of the coupled moiety includes the percentage of the moiety coupled onto surface of a particular type of binding partner or a plurality of binding partners. When a plurality of binding partners is used, the moiety can be coupled onto surface of the plurality of binding partners simultaneously or sequentially.

As used herein, "the moiety to be manipulated is completely coupled onto surface of the binding partner" means that at least 90% of the moiety to be manipulated is coupled onto surface of the binding partner in the bead. Preferably, at least 91%, 92%, 93%, 94%, 95%, 96%, 97%, 98%, 99% or 100% of the moiety to be manipulated is coupled onto surface of the binding partner. The percentage of the coupled moiety includes the percentage of the moiety coupled onto surface of a particular type of binding partner or a plurality of binding partners. When a plurality of binding partners is used, the moiety can be coupled onto surface of the plurality of binding partners simultaneously or sequentially.

As used herein, "a means for generating a physical force for manipulating a moiety-bead complex" refers to any substance, structure or a combination thereof that is capable of generating a desirable physical force for manipulating moiety-bead complex that is introduced or placed or suspended or dissolved in a fluid or otherwise existed in a fluid. The fluid containing the moiety-bead complex is introduced or placed or is generally contained in a fluid container (e.g. a liquid container such as a beaker, an eppendorf tube, any plastic or glass tube).

As used herein, "intracellular moiety" refers to any moiety that resides or is otherwise located within a cell, i.e., located in the cytoplasm or matrix of cellular organelle, attached to any intracellular membrane, resides or is otherwise located within periplasma, if there is one, or resides or is otherwise located on cell surface, i.e., attached on the outer surface of cytoplasm membrane or cell wall, if there is one.

As used herein, "an optical labeling substance that corresponds to an entity to be synthesized on said bead" means that the entity to be synthesized on a particular bead is predetermined according to the optical labeling substance on that bead.

As used herein, "wherein said beads are sorted after each synthesis cycle according to said optical labeling substances" means that the synthetic steps or orders for making an entity on a particular bead are predetermined according to the optical labeling substance on that bead and after each synthesis cycle, the optical labeling substance on the bead is assessed for directing the next synthetic step or order.

As used herein, "sample" refers to anything which may contain a moiety to be isolated, manipulated, measured, quantified or detected by the present beads and/or methods. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target analyte or enzyme containing molecules prepared in vitro.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein the term "assessing (or assessed)" is intended to include quantitative and qualitative determination of the identity and/or amount of a moiety, e.g., a protein or nucleic acid, present in the sample or one bound to the beads or in whatever form or state. Assessment would involve obtaining an index, ratio, percentage, visual or other value indicative of the identity of a moiety in the sample and may further involve obtaining a number, an index, or other value indicative of the amount or quantity or the concentration of a moiety present in the sample or on the microdevice or in whatever form or state. Assessment may be direct or indirect and may be qualitative or quantitative.

B. Multiple-property Composite Beads

In one aspect, the present invention is directed to a bead, which bead comprises:

a) a magnetizable substance; and b) an electrically conductive substance or an optical labeling substance.

Any suitable magnetizable substance can be used in the present beads. No-limiting examples of the magnetizable substances include ferrimagnetic substance, ferromagnetic substance, paramagnetic substance or superparamagnetic substances. In a specific embodiment, the present bead comprises a paramagnetic substance, e.g., a paramagnetic metal oxide composition. Preferably, the paramagnetic metal oxide composition is a transition metal oxide or an alloy thereof. Any suitable transition metals can be used, such as iron, nickel, copper, cobalt, manganese, tantalum (Ta), zinc and zirconium (Zr). In a preferred embodiment, the metal oxide composition is $Fe_3O_4$ or $Fe_2O_3$. In another example, the magnetizable substance used in the beads of the present invention comprises a metal composition. Preferably, the metal composition is a transition metal composition or an alloy thereof such as iron, nickel, copper, cobalt, manganese, tantalum, zirconium and cobalt-tantalum-zirconium (CoTaZr) alloy.

The beads of this invention may be prepared from the available primary beads, from raw materials or from metal oxides that are encapsulated by monomers which when crosslinked form rigid, polymeric coatings as disclosed in U.S. Pat. No. 5,834,121. As used herein, "rigid" refers to a polymeric coating that cross linked to the extent that the polymeric coating stabilizes the metal oxide particle within the coating (i.e. the coating essentially does not swell or dissolve) so that the particle remains enclosed therein. As used herein, "microporous" refers to a resinous polymeric matrix that swells or expands in polar organic solvent. As used herein, "load" is used to mean the capacity of the bead for attachment sites useful for functionalization or derivatization.

Suitable substances which may be incorporated as magnetizable materials, for example, include iron oxides such as magnetite, ferrites of manganese, cobalt, and nickel, hematite and various alloys. Magnetite is the preferred metal oxide. Frequently, metal salts are taught to be converted to metal oxides then either coated with a polymer or adsorbed into a bead comprising a thermoplastic polymer resin having reducing groups thereon. When starting with metal oxide particles to obtain a hydrophobic primary bead, it is necessary to provide a rigid coating of a thermoplastic polymer derived from vinyl monomers, preferably a cross-linked polystyrene that is capable of binding or being bound by a microporous matrix. Magnetic particles may be formed by methods known in the art, e.g., procedures shown in Vandenberge et al., *J. of Magnetism and Magnetic Materials,* 15–18:1117–18 (1980); Matijevic, *Acc. Chem. Res.,* 14:22–29 (1981); and U.S. Pat. Nos. 5,091,206; 4,774,265; 4,554,088; and 4,421,660. Examples of primary beads that may be used in this invention are shown in U.S. Pat. Nos. 5,395,688; 5,318,797; 5,283,079; 5,232,7892; 5,091,206; 4,965,007; 4,774,265; 4,654,267; 4,490,436; 4,336,173; and 4,421,660. Or, primary beads may be obtained commercially from available hydrophobic or hydrophilic beads that meet the starting requirements of size, sufficient stability of the polymeric coating to swelling in solvents to retain the paramagnetic particle, and ability to adsorb or absorb the vinyl monomer used to form the enmeshing matrix network. Preferably, the primary bead is a hydrophobic, polystyrene encapsulated, paramagnetic bead. Such polystyrene paramagnetic beads are available from Dynal, Inc. (Lake Success, N.Y.), Rhone Poulonc (France), and SINTEF (Trondheim, Norway). The use of toner particles or of magnetic particles having a first coating of an unstable polymer which are further encapsulated to produce an exterior rigid polymeric coating is also contemplated.

Any suitable electrically conductive substance can be used in the present beads. In a specific embodiment, the electrically conductive substance used in the present beads is gold, silver or other metal compositions, carbon material or a conductive polymer, e.g., a polyaniline, a polypyrrole, or a polythiophene. Preferably, the electrically conductive substance allows the bead to exhibit positive dielectrophoresis force. Metal materials or compositions may be incorporated into the beads by, for example, sputtering or evaporating onto the beads. Conductive polymers may be incorporated onto the bead surfaces via chemical binding or polymerization. Carbon can be cladded onto the surface of metal oxide to make it conductive.

Any suitable optical labeling substance can be used in the present beads. In specific embodiments, the optical labeling substance used in the present beads is a fluorescent substance, a scattered-light detectable particle (See e.g. U.S. Pat. No. 6,214,560) and a quantum dot (See e.g., U.S. Pat. No. 6,252,664).

Any suitable quantum dot can be used in the present beads. In a specific embodiment, the quantum dot used in the present beads comprises a Cd-X core, X being Se, S or Te. Preferably, the quantum dot can be passivated with an inorganic coating shell, e.g., a coating shell comprising Y-Z, Y being Cd or Zn, and Z being S or Se. Also preferably, the quantum dot can comprise a Cd-X core, X being Se, S or Te, a Y-Z shell, Y being Cd or Zn, and Z being S or Se, and the bead can further be overcoated with a trialkylphosphine oxide.

Any suitable methods can be used to make the CdX core/YZ shell quantum dots water-soluble (See e.g., U.S. Pat. No. 6,252,664). One method to make the CdX core/YZ shell quantum dots water-soluble is to exchange this overcoating layer with a coating which will make the quantum dots water-soluble. For example, a mercaptocarboxylic acid may be used to exchange with the trialkylphosphine oxide coat. Exchange of the coating group is accomplished by treating the water-insoluble quantum dots with a large excess of neat mercaptocarboxylic acid. Alternatively, exchange of the coating group is accomplished by treating the water-insoluble quantum dots with a large excess of mercaptocarboxylic acid in $CHCl_3$ solution (Chan and Nie, *Science,* 281:2016–2018 (1998)). The thiol group of the new coating molecule forms Cd (or Zn)—S bonds, creating a coating which is not easily displaced in solution. Another method to make the CdX core/YZ shell quantum dots water-soluble is by the formation of a coating of silica around the dots (Bruchez et al., *Science,* 281:2013–2015 (1998)). An extensively polymerized polysilane shell imparts water solubility to nanocrystalline materials, as well as allowing further chemical modifications of the silica surface. Generally, these "water-soluble" quantum dots require further functionalization to make them sufficiently stable in an aqueous solution for practical use in a fluorescence detection system (See e.g., U.S. Pat. No. 6,114,038), particularly when exposed to air (oxygen) and/or light. Water-soluble functionalized nanocrystals are extremely sensitive in terms of detection, because of their fluorescent properties (e.g., including, but not limited to, high quantum efficiency, resistance to photobleaching, and stability in complex aqueous environments); and comprise a class of semiconductor nanocrystals that may be excited with a single peak wavelength of light resulting in detectable fluorescence emissions of high quantum yield and with discrete fluorescence peaks (e.g., having a narrow spectral band ranging between about 10 nm to about 60 nm).

The quantum dot used in the present bead can have any suitable size. For example, the quantum dot can have a size ranging from about 1 nm to about 100 nm.

The bead of the present invention can comprise a single quantum dot. Alternatively, the bead of the present invention can comprise a plurality of quantum dots. Preferably, the bead of the present invention comprises at least two quantum dots that have different sizes and/or different colors. Details of quantum dots and how they can be incorporated into microbeads may be found in the literatures, for example, in the articles by Chan and Nie, *Science,* 281:2016 (1998) and by Han et al., *Nature Biotechnology,* 19:631–635 (2001).

The bead of the present invention can comprise a single optical labeling substance. Alternatively, the bead of the present invention can comprise a plurality of optical labeling substances. Preferably, the bead of the present invention comprises at least two different types of optical labeling substances.

In a specific embodiment, the bead of the present invention comprises a magnetizable substance and an electrically conductive substance. In another specific embodiment, the bead of the present invention comprises a magnetizable substance and an optical labeling substance.

The bead of the present invention can further comprise a binding partner that is capable of binding to a moiety to be isolated, manipulated or detected. Preferably, the binding partner specifically binds to the moiety. Any suitable binding partner can be used in the present bead, e.g., a cell, a cellular organelle, a virus, a molecule and an aggregate or complex thereof.

In a preferred embodiment, the bead of the present invention comprises a magnetizable substance, an electrically conductive substance and an optical labeling substance. The magnetizable substance in this preferred embodiment may be selected from groups of ferrimagnetic, ferromagnetic and paramagnetic substances. In another preferred embodiment, the bead of the present invention comprises a ferrimagentic, ferromagnetic or paramagnetic substance, an electrically conductive substance and a quantum dot. This preferred bead can further comprise a binding partner that is capable of binding to a moiety to be isolated, manipulated or detected. Preferably, the binding partner specifically binds to the moiety. Any suitable binding partner can be used in the present bead, e.g., a cell, a cellular organelle, a virus, a molecule and an aggregate or complex thereof. In still another preferred embodiment, the bead of the present invention comprises a magnetic or paramagnetic core coated with an electrically conductive substance, a quantum dot and binding partner that is capable of binding to a moiety to be isolated, manipulated or detected.

The bead of the present invention can have any suitable size. In a specific embodiment, bead of the present invention has a size ranging from about 0.02 µm to about 500 µm. Preferably, bead of the present invention has a size ranging from 0.1 µm to about 100 µm. Still preferably, bead of the present invention has a size ranging from 0.3 µm to about 20 µm.

The bead of the present invention can have any suitable shape. In a specific embodiment, the bead of the present invention has a spherical, a elliptical-sphere, cubical or other regular or irregular shape.

C. Methods, Kits and Apparatuses for Isolating, Manipulating and Detecting Moieties In another aspect, the present invention is directed to a method for isolating a moiety, which method comprises: a) providing a bead comprising 1) a magnetizable substance, 2) an optical labeling substance, and preferably 3) a binding partner that is capable of binding to a moiety to be isolated; b) contacting a sample containing or suspected of containing of said moiety with said bead provided in step a) under conditions allowing binding between said moiety and said bead or binding partner; and c) recovering said isolated bead from said sample, whereby the identity of said isolated moiety is assessed by analyzing said optical labeling substance comprised in said bead. Preferably, the binding partner specifically binds to the moiety. The present method can further comprise a step of assessing or confirming whether a moiety has been isolated and bound to the bead by analyzing a property of the moiety. For example, if the moiety to be isolated is a biological cell, the step of assessing or confirming whether a cell has been isolated and bound to the bead may comprise examining the presence of a cell on the bead with various methods, for example, optical microscopy analysis. In another example, the moiety to be isolated is a molecule that may be labeled, for example, by a fluorescent molecule. In this example, the step of assessing or confirming whether a molecule has been isolated and bound to the bead may comprise examining the presence of certain fluorescent signals on the bead with various methods, for example, by fluorescent microscopy analysis.

The above isolation methods may further comprise a step of recovering said isolated moiety from said bead by certain cleavage methods. For example, depending on the nature of binding between said moiety and said beads or binding partner, optical or chemical, or thermal cleavage methods may be utilized.

Any suitable optical labeling substance can be used in the present method. In a specific embodiment, the optical labeling substance used in the present method is a fluorescent substance, a scattered-light detectable particle (See e.g., U.S. Pat. No. 6,214,560) and a quantum dot (See e.g., U.S. Pat. No. 6,252,664). Preferably, the optical labeling substance used in the present method is a quantum dot. Any suitable quantum dot, including the quantum dot described in the above Section B can be used.

Any moiety can be isolated by the present method. For example, the moiety to be isolated can be a cell, a cellular organelle, a virus, a molecule and an aggregate or complex there of.

The bead can be recovered from the sample by any suitable methods, e.g., by a magnetic field/force using, for example, a permanent magnet or an electromagnetic chip centrifugation, dielectrophoresis collection on a dielectrophoresis chip or filtration.

Although the present method can be used to isolate a single type of moiety, it is preferably to be used in high throughput analysis and preferably a plurality of types of moieties are isolated by using a plurality of types of beads, each type of the beads is capable of binding to a member of said plurality of types of the moieties or each type of the beads contains a binding partner that is capable of binding to a member of said plurality of types of the moieties.

A moiety in any suitable sample can be isolated. Preferably, the moiety to be isolated is contained in a fluid sample.

The isolation can be conducted in any suitable apparatus or device. For example, the isolation can be conducted in a liquid container such as a beaker, a flask, a cylinder, a test tube, a microcentrifuge tube, a centrifugation tube, a culture dish, a multiwell plate and a filter device or membrane. In these non-chip formats of moiety isolation, magnetic field (for magnetic force-based isolation) and/or electric field (for electric force-based isolation) is generated in the liquid container via various means. For example, permanent magnet may be applied to the liquid container to induce magnetic field. Electrodes such as conductive wires may be introduced into the liquid container to generate electric fields. Alternatively, the isolation can be conducted in a chip format.

The method can further comprise a step of recovering said isolated moiety from said bead, by any suitable methods, e.g., by optical, chemical or other cleavage methods.

In still another aspect, the present invention is directed to a method for manipulating a moiety, which method comprises: a) providing a bead comprising 1) a magnetizable substance, 2) an electrically conductive substance, and preferably 3) a binding partner that is capable of binding to a moiety to be manipulated; b) coupling said moiety to said bead provided in step a) via binding between said moiety and said bead and/or said binding partner to form a moiety-bead complex; and c) manipulating said moiety-bead complex with a dielectrophoresis, a traveling-wave dielectrophoresis and/or a magnetic force, in a chip or non-chip format, thereby said moiety is manipulated. Preferably, the binding partner specifically binds to the moiety.

When conducted in a non-chip format, the manipulation can be conducted in any suitable apparatus or device. For example, the manipulation can be conducted in a liquid container such as a beaker, a flask, a cylinder, a test tube, a microcentrifuge tube, a centrifugation tube, a culture dish, a multiwell plate and a filter device or membrane. In these non-chip formats of moiety manipulation, magnetic field (for magnetic force-based manipulation) and/or electric field (for electric force-based manipulation) is generated in the liquid container via various means. For example, permanent magnet may be applied to the liquid container to induce magnetic field. Electrodes such as conductive wires may be introduced into the liquid container to generate electric fields.

When conducted in a chip format, the manipulation is effected through a combination of a structure that is external to the chip and a structure that is built-in in the chip. For example, chips and structures internal and external to the chips that are disclosed in the co-pending U.S. patent application Ser. No. 09/636,104, filed Aug. 10, 2000 and 09/679,024, filed Oct. 4, 2000, the disclosures of which are incorporated by reference in its entirety, can be used in the present method. For example, the methods can be used on silicon, silicon dioxide, silicon nitride, plastic, glass, ceramic, photoresist or rubber chips. In addition, the methods can be used on a chemchip, i.e., on which chemical reactions are carried out, a biochip, i.e., on which biological reactions are carried out, or a combination of a biochemchip.

The physical forces used in the present methods are effected through a combination of the structure that is external to the chip and the structure that is built-in in the chip. The external structures are energy sources that can be connected to the built-in structures for energizing the built-in structures to generate a physical force such as dielectrophoresis force, magnetic force, acoustic force, electrostatic force, mechanical force or optical radiation force. The built-in structures comprise a single unit or a plurality of units. Each unit is, when energized and in combination with the external structure, capable of effecting the physical force on the moiety-bead complex. In the case of a plurality of units, the built-in structure may further comprise the means for selectively energizing any one of the plurality of units.

In one example, when magnetic force is used to manipulate a complex of a moiety (e.g., DNA molecules) and a bead comprising its binding partner, the electromagnetic chip disclosed in the co-pending U.S. Pat. No. 6,355,491, which is incorporated by reference in its entirety, can be used in the methods. Typically, such electromagnetic chips with individually addressable micro-electromagnetic units comprise: a substrate; a plurality of micro-electromagnetic units on the substrate, each unit capable of inducing a magnetic field upon application electric current; a means for selectively energizing any one of a plurality of units to induce a magnetic field therein. Preferably, the electromagnetic chips further comprise a functional layer coated on the surface of the chips for immobilizing certain types of molecules. In this example of magnetic manipulation of moiety-binding partner-bead complexes, microelectromagnetic units are the built-in structures internal to the chip and the electrical current source that is connected to the microelectromagnetic units is the structures external to the chip. When the electric current from the external current source is applied to the microelectromagnetic units, magnetic fields will be generated in the regions around the microelectromagnetic units and magnetic forces will be produced on magnetic particles that are present in the region around the microelectromagnetic units. Typically, for the case of the manipulation force being magnetic force, the built-in structures are electromagnetic units that are incorporated on the chip and the external structures are the electrical signal sources (e.g., current sources). When the appropriately designed and fabricated electromagnetic units are energized by the electrical signal sources, magnetic fields are generated in the regions around the chip. When the bead-binding partner-moiety complexes are subjected to such magnetic fields, magnetic forces are produced on them, and such forces are dependent on the magnetic field distribution, the magnetic properties of the beads or the binding partner or bead-binding partner-moiety complexes and the magnetic properties of the medium that surrounds the beads or bead-binding partner-moiety complexes.

In another example, when dielectrophoresis force and traveling-wave dielectrophoresis force are used to manipulate a complex of a moiety (e.g., protein molecules) and its binding partner coupled onto a bead (e.g., antibodies can be coupled onto beads' surfaces, allowing for binding of protein molecules), a spiral electrode array on a glass chip, together with a phase-quardrature AC electrical signal source, can be used in the method (see "Dielectrophoretic manipulation of cells using spiral electrodes by Wang, X-B. et al., in *Biophys. J.* Volume 72, pages 1887–1899, 1997"). In this example of dielectrophoretic manipulation of moiety-binding partner-bead complexes, a spiral electrode array is a built-in structure internal to the chip and the AC electrical signal source that is connected to the spiral electrodes is the structure external to the chip. When AC electrical signals of appropriate phases from the external signal source are applied to the spiral electrode array, electrical fields will be generated in the regions around the spiral electrode array. Dielectrophoretic and traveling-wave dielectrophoretic forces will be produced on moiety-binding partner-bead complexes that are present in the region around the spiral electrode array. Typically, for the case of the manipulation force being dielectrophoresis and/or dielectrophoresis force, the built-in structures are the electrode elements and electrode arrays that are incorporated on a chip and the external structures are electrical signal sources. When the appropriately designed electrode elements and electrode arrays are energized by the electrical signal sources, non-uniform electrical fields are generated in the regions around the chip. When the bead or bead-binding partner-moiety complexes are subjected to such non-uniform electrical fields, dielectrophoresis and/or traveling-wave dielectrophoresis forces acting on the beads or bead-binding partner-moiety complexes are produced. Such forces are dependent on the interaction between the electrical field distributions and field induced dielectric polarization in beads, bead-moiety complex, or bead-binding partner-moiety complex, etc.

Any moiety including the moieties disclosed in the above Section B can be manipulated by the present method. For example, the moiety to be manipulated can be a cell, a cellular organelle, a virus, a molecule and an aggregate or complex thereof.

The present method can be used for any type of suitable manipulation. Exemplary manipulations include transportation, focusing, enrichment, concentration, aggregation, trapping, repulsion, levitation, separation, fractionation, isolation and linear or other directed motion of the moiety.

In a preferred embodiment, the moiety is not directly manipulatable by a dielectrophoresis, a traveling-wave dielectrophoresis and/or a magnetic force. In another preferred embodiment, neither the moiety nor the binding partner is directly manipulatable by a dielectrophoresis, a traveling-wave dielectrophoresis and/or a magnetic force.

Although the present method can be used to manipulate a single type of moiety, it is preferably to be used in a high throughput analysis and preferably a plurality types of moieties is manipulated. Preferably, the plurality types of moieties is manipulated via a plurality types of corresponding beads. The plurality types of moieties can be manipulated sequentially or simultaneously.

The present method can further comprise a step of recovering said manipulated moiety from said bead and/or said chip.

In a preferred embodiment, the bead used in the present method comprises an optical labeling substance and the method further comprises a step of assessing the identity of the manipulated moiety by analyzing the optical labeling substance comprised in the bead. In specific embodiments, the optical labeling substance used in the present beads is a fluorescent substance, a scattered-light detectable particle (See e.g., U.S. Pat. No. 6,214,560) and a quantum dot (See e.g., U.S. Pat. No. 6,252,664). More preferably, the optical labeling substance is a quantum dot.

In another preferred embodiment, the bead used in the present method comprises an optical labeling substance and the method further comprises a step of assessing the identity of the manipulated moiety by analyzing the optical labeling substance comprised in the bead. More preferably, the optical labeling substance is a quantum dot.

In yet another aspect, the present invention is directed to a kit for manipulating a moiety, which kit comprises: a) a bead comprising 1) a magnetizable substance, 2) an electrically conductive substance or an optical labeling substance, and preferably 3) a binding partner that is capable of binding, or capable of specifically binding, to a moiety to be manipulated; and b) a means for generating a physical force for manipulating said moiety-bead complex. Preferably, the bead comprises an optical labeling substance, e.g., a quantum dot.

In the above-mentioned kit, the means for generating a physical force for manipulating said moiety-bead complex refers to any substance, structure or a combination thereof that is capable of generating a desirable physical force for manipulating moiety-bead complex that is placed in a fluid or otherwise existed in a fluid. The fluid containing the moiety-bead complex is introduced or placed or is generally contained in a fluid container (e.g. a liquid container such as a beaker, an eppendorf tube, any plastic or glass tube). For example, when the physical force for manipulation is a magnetic force, a permanent magnet in suitable form may be part of the kit for generating magnetic field in a liquid container. In another example, when the physical force for manipulation is an electrical force, electrodes in suitable configuration may be part of the kits for generating electric field in a liquid container.

In yet another aspect, the present invention is directed to a kit for manipulating a moiety, which kit comprises: a) a bead comprising 1) a magnetizable substance, 2) an electrically conductive substance or an optical labeling substance, and preferably 3) a binding partner that is capable of binding, or capable of specifically binding, to a moiety to be manipulated; and b) a chip on which a moiety-bead complex can be manipulated. Preferably, the kit further comprises an instruction(s) for coupling the moiety to the bead and/or for manipulating the moiety-bead complex on the chip. Also preferably, the chip provided in the kit is in the form of a chamber that comprises a chip and that is capable of containing fluidic sample.

A chamber can be of any size or dimensions, and preferably can contain a fluid sample of between 0.001 microliter and 50 milliliters, more preferably between about 1 microliters and about 20 milliliters, and most preferably between about 10 microliters and about 10 milliliters. Preferably, a chamber comprises a chip. A chamber can comprise any suitable material, for example, silicon, glass, metal, ceramics, polymers, plastics, etc. and can be of a rigid or flexible material. Preferred materials for a chamber include materials that do not interfere with dielectrophoresis of moieties in a sample, for example, materials that do not bind charged or polarized molecules, such as silicon, certain plastics and polymers, for example, acrylic, or glass.

Chambers used in the methods of the present invention or comprised in the kits of the present invention can comprise chips, where chips are solid supports on which one or more separations, assays, or capturing procedures can be performed. A chip can comprise one or more metals, ceramics, polymers, copolymers, plastics, rubber, silicon, gels, or glass. A chip can comprise one or more flexible materials, and can comprise one or more semi-solid layers. A chip can comprise porous or non-porous materials. The micro structures or micro-scale structures such as, channels and wells and electrode elements and electromagnetic units are incorporated into or fabricated on the substrate for facilitating physical, biophysical, biological, biochemical, chemical reactions or processes on the chip. A chip can have a small thickness in one dimension and can have large sizes in the other two dimensions. The size of the major surfaces of a chip can vary considerably and have an area from about 1 $mm^2$ to about 0.25 $m^2$. Preferably, the size of the major surface of the chips useable in the present methods is from about 4 $mm^2$ to about 25 $cm^2$. The shape of the chips useable in the present methods can be regular shapes such as square, rectangular, circular, or oval, or can be irregularly shaped. Chip surfaces may be flat or may not be flat. Chips useable in the methods of the present invention can have one or more wells or one or more channels that can be etched or bored into a chip or built onto the surface of a chip.

For chambers with large volumes (up to 50 mL), chips of special geometries and configurations may have been used. The chips may be fabricated on flexible materials so that the chips can be folded to form tube like chambers. Multiple chips may be configured into a same chamber. The electrode elements may have to have certain configurations so that effective dielectrophoretic forces may be generated in the region of the interest in the chamber.

Preferably, in embodiments where the chamber comprises electrodes, they will be incorporated onto or within the chip, but this is not a requirement of the present invention. Electrodes on a chip can be of any shape, such as rectangular, castellated, triangular, circular, and the like. Electrodes can be arranged in various patterns, for example, spiral, parallel, interdigitated, polynomial, etc. Electrode arrays can be fabricated on a chip by microfabrication or micromachining methods known in the art, for example, electroplating, sputtering, photolithography or etching. Examples of a chip comprising electrodes include, but are not limited to, the dielectrophoresis electrode array on a glass substrate (e.g., Dielectrophoretic Manipulation of Particles by Wang et al., in IEEE Transaction on Industry Applications, Vol. 33, No. 3, May/June, 1997, pages 660–669), individually addressable electrode array on a microfabricated bioelectronic chip (e.g., Preparation and Hybridization Analysis of DNA/RNA from *E. coli* on Microfabricated Bioelectronic Chips by Cheng et al., Nature Biotechnology, Vol. 16, 1998, pages 541–546), and the capillary electrophoresis chip (e.g. Combination of Sample-Preconcentration and Capillary Electrophoresis On-Chip by Lichtenberg, et al., in Micro Total Analysis Systems 2000 edited by A. van den Berg et al., pages 307–310).

A chamber that comprises a chip useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, e.g., tygon or teflon or PEEK tubing. Alternatively, a port can provide an opening in a wall of a chamber for the dispensing of sample into the chamber by, for example, pipetting or injection.

Conduits that engage one or more ports of the sample can introduce a sample by any means, including a pump (for example, a peristaltic pump or infusion pump), pressure source syringe, or gravity feed. One or more reagents, buffers, or solutions, including, but not limited to, a solution that selectively modifies the dielelectric properties of one or more moieties in a sample, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

In yet another aspect, the present invention is directed to a method for detecting a moiety, which method comprises: a) providing a bead comprising 1) a magnetizable substance, 2) an optical labeling substance, and preferably 3) a binding partner that is capable of binding to a moiety to be detected; b) contacting a sample containing or suspected of containing of said moiety with said bead provided in step a) under conditions allowing binding between said moiety and said bead and/or said binding partner; and c) detecting binding between said moiety and said bead and/or said binding partner, whereby the presence or amount of said moiety is assessed by analysis of binding between said moiety and said bead and/or said binding partner and the identity of said moiety is assessed by analyzing the optical labeling substance comprised in the bead. Preferably, the binding partner specifically binds to the moiety.

Any suitable optical labeling substance, including the ones described in the above Section B, can used in the present method. In specific embodiments, the optical labeling substance used in the present beads is a fluorescent substance, a scattered-light detectable particle (See e.g., U.S. Pat. No. 6,214,560) and a quantum dot (See e.g., U.S. Pat. No. 6,252,664). Any suitable quantum dot, including the ones described in the above Section B, can used in the present method.

Any moiety including the moieties disclosed in the above Section B can be detected by the present method. For example, the moiety to be detected can be a cell, a cellular organelle, a virus, a molecule and/or an aggregate or complex thereof.

Although the present method can be used to detect a single type of moiety, it is preferably to be used in a high throughput analysis and preferably a plurality types of moieties is detected by using a plurality types of different types of beads, each type of the beads contains a binding partner that is capable of binding to a member of the plurality types of the moieties. The plurality types of moieties can be detected sequentially or simultaneously. To be used in the assay, the beads' optical encoding can correspond to the binding partner (and so moiety). Thus, each type of the beads has a unique optical encoding property and contains a specific binding partner that is capable of binding to a member of the plurality types of the moieties. Alternatively, the beads' dielectric property can correspond to the binding partner. Thus, each type of the beads has a unique dielectric property and can be manipulated or processed by an electric field of a specific condition (e.g., the bead exhibiting positive dielectrophoresis at a specific frequency). Each type of these beads can contain specific binding partners that is capable of binding to a member of the plurality types of the moieties.

The detection can be conducted in any suitable apparatus or device. For example, the detection can be conducted in a liquid container such as a beaker, a flask, a cylinder, a test tube, an enpindorf tube, a centrifugation tube, a culture dish, a multiwell plate and a filter device or membrane. Alternatively, the bead is placed or immobilized on a surface and the detection can be conducted in a chip format. Preferably, a plurality of bead is placed or immobilized on a surface and the detection can be conducted in a chip format.

A moiety in any suitable sample can be detected. Preferably, the moiety to be detected is contained in a fluid sample.

The binding between the moiety and the bead and/or binding partner can be detected by any suitable methods, devices or instruments. For example, the moiety can be labeled, e.g., with fluorescent, radioactive, enzymatic or other chemical labels. The moiety can be labeled before its binding with the bead or binding partner or after its binding with the bead or binding partner. In another example, the absorbance or other optical properties of the moiety can be used in detecting its binding with the bead or binding partner. In still another example, the molecular weight of the moiety can be used in detecting its binding with the bead or binding partner, e.g., by mass spectrometry such as MALDI-TOF. The detecting methods based on the labeling of the moiety can be conducted in a direct labeling method, i.e., the moiety to be detected is labeled, or in a competitive assay format, i.e., a labeled moiety or moiety analog is added to the sample containing a moiety to be detected. In yet another example, the moiety is cleaved off or recovered from, or isolated or purified from the moiety-bead (or binding partner) complex before the detection. Any suitable methods, e.g., HPLC, can be used to isolate or purify the moiety.

In yet another aspect, the present invention is directed to an array for detecting, isolating or manipulating moieties, which array comprises a plurality of beads of the present invention positioned, deposited or immobilized on a surface, e.g. a chip, each of said beads comprising 1) a magnetizable substance, 2) an electrically conductive substance or an optical labeling substance, and preferably 3) a binding partner that is capable of binding, or capable of specifically binding, to a moiety to be detected, isolated or manipulated.

The beads can be positioned, deposited or immobilized on the surface e.g., a chip surface, using any suitable methods such as being positioned on a surface by a magnetic force.

The present methods can be used for analyzing, isolating, manipulating or detecting any types of moieties when the moieties are involved in certain processes, such as physical, chemical, biological, biophysical or biochemical processes, etc., in a chip format or non-chip format. Moieties can be cells, cellular organelles, viruses, molecules or an aggregate or complex thereof. Moieties can be pure substances or can exist in a mixture of substances wherein the target moiety is only one of the substances in the mixture. For example, cancer cells in the blood from leukemia patients, cancer cells in the solid tissues from patients with solid tumors and fetal cells in maternal blood from pregnant women can be the moieties to be isolated, manipulated or detected. Similarly, various blood cells such as red and white blood cells in the blood can be the moieties to be isolated, manipulated or detected. DNA molecules, mRNA molecules, certain types of protein molecules, or all protein molecules from a cell lysate can be moieties to be isolated, manipulated or detected.

Non-limiting examples of cells include animal cells, plant cells, fungi, bacteria, recombinant cells or cultured cells. Animal, plant cells, fungus, bacterium cells to be isolated, manipulated or detected can be derived from any genus or subgenus of the Animalia, Plantae, fungus or bacterium kingdom. Cells derived from any genus or subgenus of ciliates, cellular slime molds, flagellates and microsporidia can also be isolated, manipulated or detected. Cells derived from birds such as chickens, vertebrates such as fish and mammals such as mice, rats, rabbits, cats, dogs, pigs, cows, ox, sheep, goats, horses, monkeys and other non-human primates, and humans can be isolated, manipulated or detected by the present methods.

For animal cells, cells derived from a particular tissue or organ can be isolated, manipulated or detected. For example, connective, epithelium, muscle or nerve tissue cells can be isolated, manipulated or detected. Similarly, cells derived from an accessory organ of the eye, annulospiral organ, auditory organ, Chievitz organ, circumventricular organ, Corti organ, critical organ, enamel organ, end organ, external female genital organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subformical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be isolated, manipulated or detected. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be isolated, manipulated or detected. Further, cells derived from any plants, fungi such as yeasts, bacteria such as eubacteria or archaebacteria can be isolated, manipulated or detected. Recombinant cells derived from any eucaryotic or prokaryotic sources such as animal, plant, fungus or bacterium cells can also be isolated, manipulated or detected. Cells from various types of body fluid such as blood, urine, saliva, bone marrow, sperm or other ascitic fluids, and subfractions thereof, e.g., serum or plasma, can also be isolated, manipulated or detected.

Isolatable, manipulatable or detectable cellular organelles include nucleus, mitochondria, chloroplasts, ribosomes, ERs, Golgi apparatuses, lysosomes, proteasomes, secretory vesicles, vacuoles or microsomes. Isolatable, manipulatable or detectable viruses include intact viruses or any viral structures, e.g., viral particles, in the virus life cycle that can be derived from viruses such as Class I viruses, Class II viruses, Class III viruses, Class IV viruses, Class V viruses or Class VI viruses.

Isolatable, manipulatable or detectable molecules can be inorganic molecules such as ions, organic molecules or a complex thereof. Non-limiting examples of ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of organic molecules include amino acids, peptides, proteins, nucleosides, nucleotides, oligonucleotides, nucleic acids, vitamins, monosaccharides, oligosaccharides, carbohydrates, lipids or a complex thereof.

Any amino acids can be isolated, manipulated or detected by the present methods. For example, a D- and a L-amino-acid can be isolated, manipulated or detected. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be isolated, manipulated or detected.

Any proteins or peptides can be isolated, manipulated or detected by the present methods. For example, membrane proteins such as receptor proteins on cell membranes, enzymes, transport proteins such as ion channels and pumps, nutrient or storage proteins, contractile or motile proteins such as actins and myosins, structural proteins, defense protein or regulatory proteins such as antibodies, hormones and growth factors can be isolated, manipulated or detected. Proteineous or peptidic antigens can also be isolated, manipulated or detected.

Any nucleic acids, including single-, double and triple-stranded nucleic acids, can be isolated, manipulated or detected by the present methods. Examples of such nucleic acids include DNA, such as A-, B- or Z-form DNA, and RNA such as mRNA, tRNA and rRNA.

Any nucleosides can be isolated, manipulated or detected by the present methods. Examples of such nucleosides include adenosine, guanosine, cytidine, thymidine and uridine. Any nucleotides can be isolated, manipulated or detected by the present methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any vitamins can be isolated, manipulated or detected by the present methods. For example, water-soluble vitamins such as thiamine, riboflavin, nicotinic acid, pantothenic acid, pyridoxine, biotin, folate, vitamin $B_{12}$ and ascorbic acid can be isolated, manipulated or detected. Similarly, fat-soluble vitamins such as vitamin A, vitamin D, vitamin E, and vitamin K can be isolated, manipulated or detected.

Any monosaccharides, whether D- or L-monosaccharides and whether aldoses or ketoses, can be isolated, manipulated or detected by the present methods. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be isolated, manipulated or detected by the present methods. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

D. Methods for Synthesizing a Library and Uses Thereof

In yet another aspect, the present invention is directed to a method for synthesizing a library, which method comprises: a) providing a plurality of beads, each of said beads comprises a magnetizable substance and an optical labeling substance that corresponds to an entity to be synthesized on said bead; and b) synthesizing said entities on said beads, wherein said beads are sorted after each synthesis cycle according to said optical labeling substances and are directed to appropriate next synthesis cycle, whereby a library is synthesized, wherein each of said beads contains an entity that corresponds to an optical labeling substance on said bead and the sum of said beads collectively contains a plurality of entities that is predetermined before the library synthesis. In this method of library synthesis, it is possible to have multiple individual beads to have same optical encoding substance. These beads having same optical encoding substance will go through same synthesis cycle and same entity will be synthesized on these beads. Furthermore, if desired, it is even possible for the beads having different encoding substance to go through same synthesis cycle and to have same synthesized entity on them.

Any suitable magnetizable substance, including the ones described in the above Section B, can be used in the present method. Preferably, paramagnetic substance comprising a metal oxide particle is used in the present method.

Any suitable optical labeling substance, including the ones described in the above Section B, can be used in the present method. In specific embodiments, the optical labeling substance used in the present beads is a fluorescent substance, a scattered-light detectable particle (See e.g., U.S. Pat. No. 6,214,560) and a quantum dot (See e.g., U.S. Pat. No. 6,252,664). Preferably, the optical labeling substance used in the present method is a quantum dot. Any suitable quantum dot, including the ones described in the above Section B, can be used in the present method.

The bead used in the present method can further comprise an element that facilitates and/or enables manipulation of the bead and/or a moiety/bead complex (See e.g, co-pending U.S. patent application Ser. Nos. 09/636,104, filed Aug. 10, 2000; 09/679,024, filed Oct. 4, 2000; and 09/924,428, filed Aug. 7, 2001, published as U.S. patent application Ser. No. 20020137059A1). Any suitable element can be used. For example, the element can be a cell, a cellular organelle, a virus, a microparticle, an aggregate or complex of molecules and an aggregate or complex thereof. The element can facilitate and/or enable manipulation of the bead and/or a moiety/bead complex by any suitable physical force such as a dielectrophoresis, a traveling-wave dielectrophoresis, a magnetic, an acoustic, an electrostatic, a mechanical, an optical radiation and a thermal convection force. For example, the element can be a conductive or insulating material for manipulation by a dielectrophoresis force, a material with high or low acoustic impedance for manipulation by a acoustic force or a charged material for manipulation by an electrostatic force.

Although the bead used in the present method can comprise a single element, it can also be used in a high throughput analysis and can comprise a plurality of the elements, each of the elements facilitates and/or enables manipulation of the bead and/or the moiety/bead complex by a different physical force.

Any number of suitable entity(ies) can be synthesized on a single bead. For example, a single entity or a plurality of entities can be synthesized on a single bead. Preferably, a single entity is synthesized on a single bead.

The present method can be used to synthesize any kind of library. For example, the synthesized entities can be peptides, proteins, oligonucleotides, nucleic acids, vitamins, oligosaccharides, carbohydrates, lipids, small molecules, or a complex or combination thereof. Preferably, the synthesized library comprises a defined set of entities that are involved in a biological pathway, belongs to a group of entities with identical or similar biological function, expressed in a stage of cell cycle, expressed in a cell type, expressed in a tissue type, expressed in an organ type, expressed in a developmental stage, entities whose expression and/or activity are altered in a disease or disorder type or stage, or entities whose expression and/or activity are altered by drug or other treatments.

In a specific embodiment, the synthesized library comprises a defined set of nucleic acid, e.g., DNA or RNA, fragments such as a defined set of nucleic acid fragments that cover an entire genome, e.g., the entire human genome sequence. Preferably, each of the nucleic acid fragments in the synthesized library comprises at least 10, 15, 20, 25, 50, 75, 100, 200, or 500 nucleotides.

In another specific embodiment, the synthesized library comprises a defined set of protein or peptide fragments such as a defined set of protein or peptide fragments that cover protein or peptide sequences encoded by an entire genome, e.g., the entire human genome sequence. Preferably, each of the protein or peptide fragments in the synthesized library comprises at least 5, 10, 15, 20, 25, 50, 75, 100, 150, 200, 300, 400 or 500 amino acid residues.

In still another specific embodiment, a library that is synthesized according to the above-described method is provided.

In yet another specific embodiment, a method for generating an antibody library is provided, which method comprises: a) contacting a library synthesized by the above-described method with a plurality of antibodies; and b) selecting and/or recovering the antibodies that specifically bind to the entities of the library synthesized according to the above-described method. Any suitable. antibodies can be used in the present method. For example, plurality of antibodies used in the present method is a phage display library (See U.S. Pat. Nos. 6,127,132 and 6,174,708).

In yet another aspect, the present invention is directed to a method for synthesizing a library, which method comprises: a) providing a plurality of beads, each of said beads comprising a magnetizable substance, an electrically conductive substance and a unique optical labeling substance; and b) synthesizing an entity on said beads, wherein said beads are identified after each synthesis cycle according to said unique optical labeling substances, whereby a library is synthesized, wherein each of said beads contains an entity that can be identified according to said unique optical labeling substance on each of said beads. A library that is synthesized according to the above-described method is provided. In this method of library synthesis, no two beads would have same optical labeling substance. The synthesis cycle that each bead goes through during library synthesis has been identified and recorded based on the unique optical labeling substance on each bead. Thus, the entity on each bead can be identified.

E. Preferred Embodiment

Lab-on-a-chip is a concept that revolutionizes the analytical process, featuring miniaturization, integration, and automation. Active chips, such as AVIVA Biosciences' multiple force chips, make the integration of multiple tasks, such as sample preparation, reaction, and detection possible. These active chips can utilize numerous beads as molecular carriers in the analytical process or as additional means to process cells or other biological materials. The beads can be designed to be responsive to the forces generated by the chips.

Magnetic force has been widely used for separation and analysis with magnetic beads. Magnetic beads are generally prepared by precipitation of $FeCl_3$ and $FeCl_2$ in basic solution such as NaOH or $NH_4OH$. The formed $Fe_3O_4$ particle is in the size range of about 10 nm to about 5 micrometer. These particles are coated with a layer of polymer on their surfaces, e.g., dextran. The coated polymer is further activated to bind other molecules. These particles can also be mixed with organic monomers (e.g. styrene) and initiators to formed larger-size particles after the polymerization of the monomer. In this way, $Fe_3O_4$ particles are encapsulated in the organic polymer beads, e.g., polystyrene beads. The formed larger particles can be further coated and modified on the surface to bind other molecules. Modified magnetic particles can be used to bind interested moieties and conveniently separate them from sample matrix using a magnet. This method has been used for the separation of cells, DNA, and proteins.

Carbon particles are electrically conductive, and they have been shown to be responsive to dielectrophoretic forces and exhibit both positive and negative dielectrophoresis effects under appropriate electric field conditions. Also, the density of carbon particles is quite low, thereby making it easier to be manipulated on a flat surface. Carbon particles can be modified by oxidation and further chemical and biochemical reactions.

Quantum dots have attracted a lot of attention recently for their use as fluorescence sensing of biomolecules. Quantum dots of different sizes fluoresce at different wavelengths. Therefore, beads containing various sized quantum dots can be used to encode the beads. Bead encoding allows high throughput analysis of a large number of molecules, such as DNA and proteins. Details of quantum dots and how they can be incorporated into microbeads may be found in the literatures, for example, in the articles by Chan and Nie, *Science*, 281:2016 (1998) and by Han et al., *Nature Biotechnology*, 19:631–635 (2001).

In a preferred embodiment, composite beads comprising magnetic particles ($Fe_3O_4$), carbon particles, and quantum dots are prepared. The composite beads are further modified for the conjugation of biomolecules and their use for high throughput analyses are illustrated.

First, nanometer size (10 to 100 nm) magnetic particles are prepared by reaction of $FeCl_3$ and $FeCl_2$ with NaOH. These particles are added to the polymerization mixture of urea and formaldehyde solution at pH of about 2.0. As a result, spherical beads with about 5 micrometer size are obtained. Second, carbon particles, polyaniline, quantum dots, and above magnetic beads are added to a new urea-formaldehyde polymerization mixture at pH of about 2.0. Uniform spherical composite beads with the size of about 6 micrometer are obtained. Third, these new beads are coated with a crosslinked layer of functional group containing polymer, and these functional groups are useful for conjugating special molecules for further affinity bindings.

The prepared beads possess multiple properties that can be used for many purposes, but in this specific embodiment, we emphasize their use with the multiple force chips for the separation and analysis of multiple analytes. The exemplary uses include cell separation, e.g., fetal and cancer cells separation, mRNA extraction, DNA extraction, protein extraction and separation, DNA analysis, protein analysis, drug discovery and screening and other bioassays.

F. EXAMPLES

Example One

In the First Example, Multiple Property Beads with Both Magnetizable Property and Electronic Conductive Properties were Produced Fifteen grams $FeSO_4 \cdot 7H_2O$ and 60 g $Fe_2(SO_4)_3 \cdot XH_2O$ were added to 250 ml de-ionized (DI) $H_2O$ in a flask, the mixture was heated to 90° C. with stirring, then 220 ml of 6 N NaOH were added to the flask, while keep stirring for 45 minutes. After the mixture was cooled down, the mixture was centrifuged at 2,500 RPM for 15 minutes. The supernatant was removed and the pellet was re-suspended in DI $H_2O$. This centrifuge step was repeated for three times. The pellet was collected in the final wash and was dispersed into 250 ml of 10% perchloric acid. This suspension was shaken and the pH was adjusted to 1.9, then 3.5 g urea and 5.6 g formaldehyde were added, mixed well, let sit. After 30 minutes, the magnetic beads formed were separated from the liquid by a magnet. The beads were washed three times with $H_2O$.

The magnetic beads prepared above were dispersed in propanol, carbon colloidal was added to the suspension, and the mixture was vortexed for 3 minutes, then the particle was collected with a magnet and the liquid was decanted. The beads were washed with $H_2O$. Finally, the beads were dispersed in DI $H_2O$.

Figure 2:
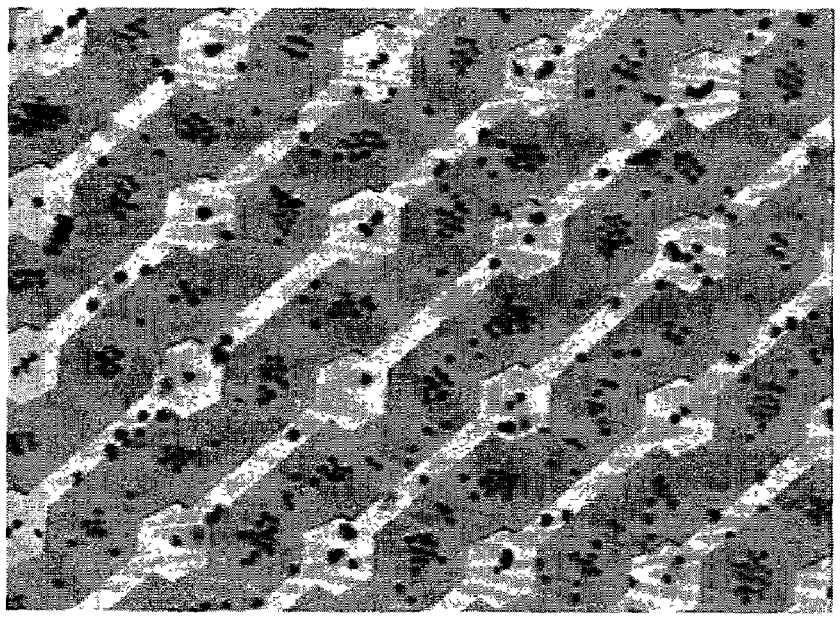
FIG. 2 shows the collection and aggregation of the microbeads at the interspaces between the neighboring electrodes under an electric voltage of 5 V peak-peak (pk-to-pk) at frequency of 50 kHz. The microbeads are seen as black dots, the microelectrodes are seen as the light structure and the grey area represents the inter-microelectrode space.
Figure 3:
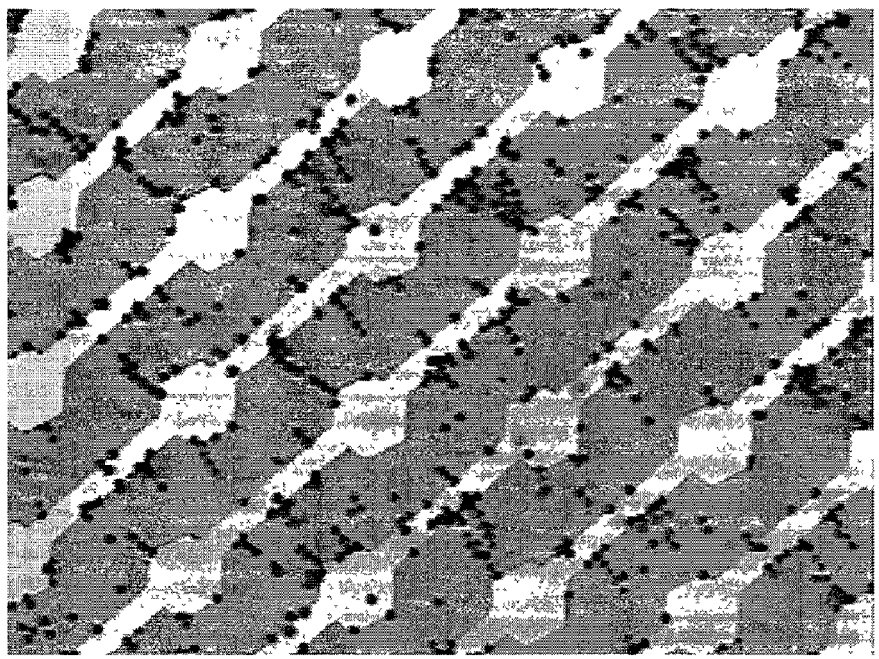
FIG. 3 shows the collection and aggregation of the microbeads at the electrode edges between the neighboring electrodes under an electric voltage of 5 V pk-to-pk at frequency of 500 kHz. The microbeads are seen as black dots, the microelectrodes are seen as the light structure and the grey area represents the inter-microelectrode space.

The microbeads prepared above were tested for their dielectric and magnetic properties. To investigate their dielectric properties, the beads were suspended in an aqueous solution having an electric conductivity of ~10 µS/cm. The microbeads were then tested for their dielectrophoretic responses. FIG. 1 shows the random distribution of the microbeads on a microelectrode array. When an electric voltage of 5 V peak-to-peak (pk-to-pk) at frequency of 50 kHz was applied to the electrodes, the microbeads moved towards the interspaces between the neighboring electrodes where the electric field strength was minimum or weak (FIG. 2). The microbeads at these frequencies were less polarizable than that of the suspending medium, exhibiting a negative dielectrophoresis. On the other hand, when an electric voltage of 5 V pk-to-pk at frequency of 500 kHz was applied to the electrodes, the microbeads moved towards the electrode edges where the electric field strength was maximum or strongest (FIG. 3). The microbeads at these frequencies were more polarizable than that of the suspending medium, exhibiting a positive dielectrophoresis. As shown below, these microbeads can be further manipulated by a magnetic field. Clearly, these microbeads have unique compositions as well as unique properties so that they can be manipulated not only by magnetic field but also by AC electrical field to exhibit both positive dielectrophoresis (DEP) and negative DEP. Typically, commercially available magnetic beads exhibit magnetic field responses with none or small negative dielectrophoresis behavior.

Figure 4:
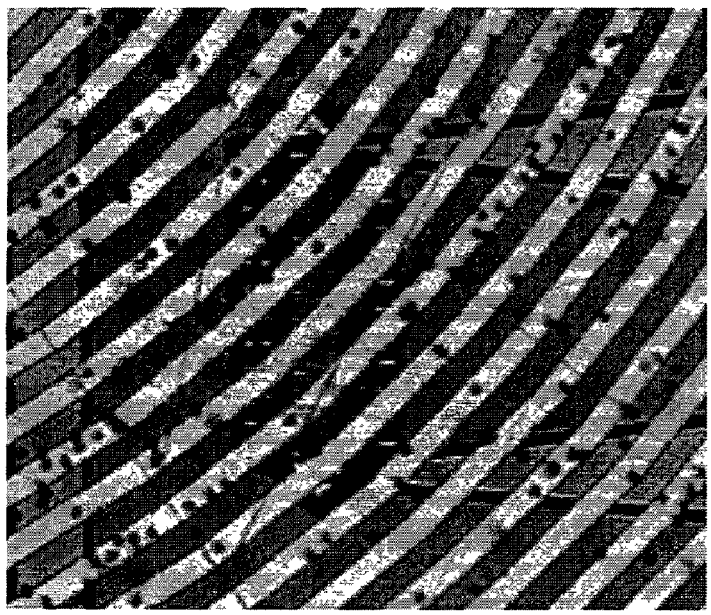
FIG. 4 shows the random distribution of the microbeads on an electromagnetic chip. The microbeads are seen as black dots, the dielectrophoretic force generating structures are seen as the light structures and the electromagnetic coil is seen as the dark structure underneath the dielectrophoretic force generating structures.

In another test, the microbead suspension was introduced over an electrical magnetic chip on which the multiple electromagnetic coil/units are incorporated. FIG. 4 shows the random distribution of the microbeads on an electromagnetic chip. In this example, the chip used for beads-testing comprises both magnetic elements as well as microelectrode elements so that the microelectrode elements can be used for dielectrophoretic manipulation of the microbeads while the magnetic elements are used for magnetic manipulation of the microbeads.

Figure 5:
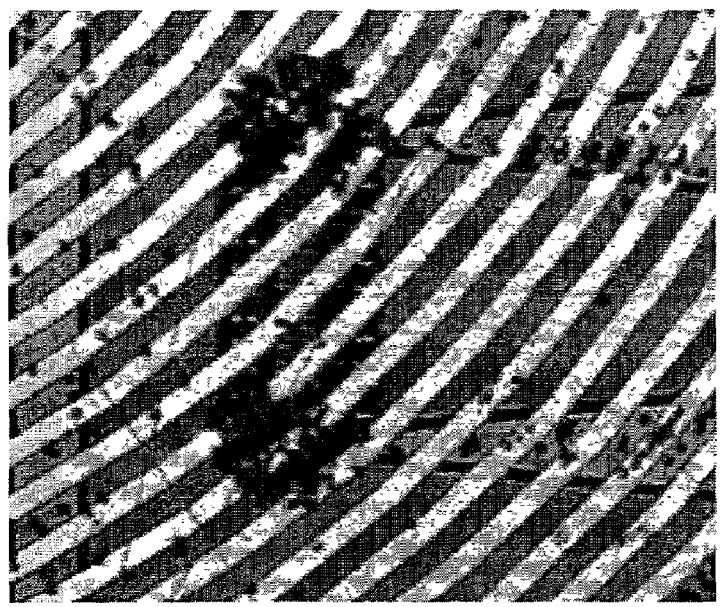
FIG. 5 shows that the microbeads were attracted towards the poles of the electromagnetic units when a DC current of 200 mA was applied to an electromagnetic unit on the chip. The microbeads are seen as black dots, the dielectrophoretic force generating structures are seen as the light structures and the electromagnetic coil is seen as the dark structure underneath the dielectrophoretic force generating structures.
Figure 6:
FIG. 6 shows that the collection of the microbeads at the poles of the electromagnetic units after the DC current has been applied for over 2 minutes. The microbeads are seen as black dots, the dielectrophoretic force generating structures are seen as the light structures and the electromagnetic coil is seen as the dark structure underneath the dielectrophoretic force generating structures.

When a DC current of 200 mA was applied to an electromagnetic unit on the chip, the microbeads at its neighborhood were attracted towards the poles of the electromagnetic units (FIG. 5). The applied DC current resulted in a magnetic field generated around this unit. The microbeads, because of their magnetic particles incorporated inside, responded to the magnetic field and were caused to move towards the poles of the magnetic units where the magnetic field was strongest. With time during the process of magnetic collection/manipulation, more and more magnetic microbeads were collected at the poles of the electromagnetic units. Such collection of the microbeads at the poles of the electromagnetic units (FIG. 6) clearly demonstrates that the microbeads possess magnetic materials or magnetizable materials so that the microbeads can interact with and be manipulated and/or processed by magnetic field.

Example Two

In This Example, Microbeads were Produced with Magnetizable Properties

A 100 mL three neck flask was equipped with a mechanical stirrer, a condenser, a thermometer and an argon inlet. Ten mL of iron oxide colloid solution (see above) and 10 mL of DI water were added to the flask. The liquid was stirred under argon. Thirty mg of benzoyl peroxide (BPO) were dissolved in 1 mL of mixture of styrene and divinyl benzene (DVB) (9:1, V/V) to form monomer solution. The monomer mixture was added to the colloid solution, stirred at room temperature under argon for 20 minutes, and then stirred under argon atmosphere at 55° C. for 16–20 hours. The reaction mixture was filtered through two layers of cheese cloth, and the filtrate was magnetically decanted (2 minutes magnetic decantation). The magnetic particles were resuspended in DI water and magnetic decantation (1–2 minutes) was performed. The wash step was repeated until the decanted liquid became clear.

Magnetic particles suspension (containing about 300 mg of particles) was added to a 100 mL flask, and the suspension was diluted with water to 50 mL volume. Thirty mg of sodium dodecyl sulfate (SDS) and 300 mg of potassium persulfate (KPS) were added to the particle suspension, shaken until SDS and KPS were completely dissolved.

A monomer solution was made by mixing 0.09 mL of styrene, 0.03 mL of DVB, and 0.06 mL of undecylenic acid in 0.6 mL of methanol. The monomer solution was added to the particle suspension, and the flask was sealed with rubber septa. The flask was evacuated with a vacuum pump for 10 minutes, and shaken (250 rps) at 55° C. for 5 hours. The reaction solution was magnetically decanted. The coated magnetic particles were resuspended in DI water and magnetic decantation was performed.

Example Three

In this Example, Streptavidin Bonded Magnetic Microbeads were Produced

Magnetic beads were dispersed in DI water (40 mL), 0.5 mL of 20% SDS solution was added to above beads solution, shaken with Vortex shaker for 10 seconds, sonicated for 2 min., and liquid was separated from beads using a 50 mL magnetic separator. The beads were dispersed in 2-(N-morpholino)-ethane sulfonic acid (MES) buffer (0.1 M, pH 4.7), and 0.1 g 1-ethyl-3-(3-dimethylaminopropyl)-carbodiimide hydrochloride (EDC) and 0.05 g Sulfo-NHS (N-hydroxysuccinimide 3-sulfonic acid) were added to this solution, shaken with Vortex shaker for 10 seconds, and shaken on a plate shaker for 2 hours. The beads were washed with MES buffer. The beads were then dispersed in phosphate-buffered saline (PBS buffer), 0.5 mL of 2,2'-(ethylenedioxy) bis(ethylamine) was added to this solution, vortexed for 10 seconds and shaken on a plate shaker for 2 hours. After that, the beads were washed with PBS buffer. Again, the beads were dispersed in PBS buffer (35 mL), 0.5 mL of glutaric dialdehyde was added to the beads, shaken for 1 hour. The beads were washed with PBS buffer, and dispersed in PBS buffer. Streptavidin (2 mg in water) and 10 mg of sodium cyanoborohydride were added to the dispersed beads, shaken on a plate shaker for 2 hours. After that, 5 mg of sodium cyanoborohydride were added, shaken for another 1 hour. The beads were washed with PBS buffer. The beads were stored in PBS buffer containing 1% Tween 20, 0.5% bovine serum albumin (BSA) and 0.02% sodium azide.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A bead, which bead comprises:
    a) a magnetizable substance; and
    b) an electrically conductive substance, and
    an optical labeling substance selected from the group consisting of a fluorescent substance, a scattered-light detectable particle and a quantum dot;
    wherein the bead has a size of at least 0.1 µm.

2. The bead of claim 1, wherein the quantum dot comprises a Cd-X core, X being Se, S or Te.

3. The bead of claim 2, wherein the quantum dot is passivated with an inorganic coating shell.

4. The bead of claim 3, wherein the coating shell comprises Y-Z, Y being Cd or Zn, and Z being S or Se.

5. The bead of claim 1, wherein the quantum dot comprises a Cd-X core, X being Se, S or Te, a Y-Z shell, Y being Cd or Zn, and Z being S or Se, and the bead is further overcoated with a trialkylphosphine oxide.

6. The bead of claim 1, which further comprises a plurality of optical labeling substances.

7. The bead of claim 6, which comprises at least two different types of optical labeling substances.

8. The bead of claim 1, which comprises a plurality of quantum dots.

9. The bead of claim 8, wherein at least two quantum dots have different sizes.

10. The bead of claim 1, wherein the quantum dot has a size ranging from about 1 nm to about 100 nm.

11. The bead of claim 1, which has a size up to about 100 µm.

12. The bead of claim 1, which has a spherical, a cubical or other regular or irregular shape.

13. The bead of claim 1, which has a magnetizable substance core coated with an electrically conductive substance, a quantum dot and a binding partner that is capable of binding to a moiety.

14. The bead of claim 1, wherein the bead has a size ranging from 0.3 µm to about 20 µm.

15. The bead of claim 1, further comprising a stable polymeric coating.

16. A bead, which bead comprises:
a) a magnetizable substance; and
b) an electrically conductive substance,
wherein the bead has a size of at least 0.1 µm,
and wherein the magnetic substance comprises a transition metal composition or alloy selected from the group consisting of cobalt, manganese, tantalum, zirconium and cobalt-tantalum-zirconium (CoTaZr) alloy.

17. The bead of claim 16, further comprising a quantum dot.

18. A bead, which bead comprises:
a) a magnetizable substance; and
b) an electrically conductive substance,
wherein the bead has a size of at least 0.1 µm,
wherein the electrically conductive substance is selected from the group consisting of gold, silver, and a conductive polymer.

19. The bead of claim 18, wherein the conductive polymer is a polyaniline, a polypyrrole, or a polythiophene.

20. A bead, which bead comprises:
a) a magnetizable substance; and
b) an electrically conductive substance,
and a binding partner that is capable of specifically binding to a moiety.

21. The bead of claim 20, wherein the binding partner is selected from the group consisting of a cell, a cellular organelle, a virus, a molecule and an aggregate or complex thereof.

22. A bead, which bead comprises:
a) a magnetizable substance; and
b) an electrically conductive substance,
and a quantum dot.

23. The bead of claim 22, which further comprises a binding partner that is capable of specifically binding to a moiety.

24. The bead of claim 23, wherein the binding partner is selected from the group consisting of a cell, a cellular organelle, a virus, a molecule and an aggregate or complex thereof.

25. A bead, which bead comprises:
a magnetizable substance; and
a quantum dot, which quantum dot comprises a Cd-X core, X being Se, S or Te, a Y-Z shell, Y being Cd or Zn, and Z being S or Se,
wherein the bead is further overcoated with a trialkylphosphine oxide.

* * * * *